US010197442B2

(12) United States Patent
Kieu

(10) Patent No.: US 10,197,442 B2
(45) Date of Patent: Feb. 5, 2019

(54) DUAL-COMB SPECTROSCOPY WITH A FREE-RUNNING BIDIRECTIONALLY MODE-LOCKED FIBER LASER

(71) Applicant: Arizona Board of Regents on Behalf of the University of Arizona, Tucson, AZ (US)

(72) Inventor: Khanh Q. Kieu, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/578,397

(22) PCT Filed: Jun. 1, 2016

(86) PCT No.: PCT/US2016/035340
§ 371 (c)(1),
(2) Date: Nov. 30, 2017

(87) PCT Pub. No.: WO2016/196677
PCT Pub. Date: Dec. 8, 2016

(65) Prior Publication Data
US 2018/0216996 A1 Aug. 2, 2018

Related U.S. Application Data

(60) Provisional application No. 62/169,200, filed on Jun. 1, 2015.

(51) Int. Cl.
*G01J 3/45* (2006.01)
*G01J 3/10* (2006.01)
(Continued)

(52) U.S. Cl.
CPC ............. *G01J 3/10* (2013.01); *G01C 19/72* (2013.01); *G01C 19/721* (2013.01); *G01J 3/42* (2013.01);
(Continued)

(58) Field of Classification Search
CPC ...... G01J 3/00; G01J 3/10; G01J 3/427; G01J 3/45; G01C 19/721; H01S 3/1106; H01S 3/1109; H01S 3/06791
See application file for complete search history.

(56) References Cited

U.S. PATENT DOCUMENTS 6,570,892 B1   5/2003 Lin et al.
6,868,098 B1 * 3/2005 Piche .................. H01S 5/065
                                                            372/107
(Continued)

OTHER PUBLICATIONS

Doddington et al., "Dual-comb spectroscopy" Optica, vol. 3, No. 4, Apr. 2006, pp. 414-426.
(Continued)

*Primary Examiner* — Jonathan Hansen
(74) *Attorney, Agent, or Firm* — Stuart H. Mayer; Mayer & Williams PC

(57) ABSTRACT

A method of interrogating an absorbing sample includes using a mode-locked laser mode-locked in both a clock-wise (CW) and a counter-clock wise (CCW) direction to generate first and second optical pulses having different repetition rates. One of the first and second optical pulses is directed in a CW direction and the other of the first and second optical pulses is directed in the CCW direction. The first optical pulses are transmitted through the absorbing sample to probe the absorbing sample while the second optical pulses are transmitted through the absorbing sample to act as a local oscillator. An interference pattern produced by interference between the first and second optical pulses is detected after traversing the absorbing sample.

26 Claims, 8 Drawing Sheets

(51) Int. Cl.

| | | |
|---|---|---|
| *G01C 19/72* | (2006.01) | |
| *H01S 3/067* | (2006.01) | |
| *H01S 3/11* | (2006.01) | |
| *G01J 3/427* | (2006.01) | |
| *H01S 3/10* | (2006.01) | |
| *H01S 3/16* | (2006.01) | |
| *G01J 3/42* | (2006.01) | |

(52) U.S. Cl.
CPC ............... *G01J 3/427* (2013.01); *G01J 3/45* (2013.01); *H01S 3/06791* (2013.01); *H01S 3/10038* (2013.01); *H01S 3/10061* (2013.01); *H01S 3/1109* (2013.01); *H01S 3/1112* (2013.01); *H01S 3/1608* (2013.01)

(56) References Cited

U.S. PATENT DOCUMENTS

| | | |
|---|---|---|
| 7,012,696 B2 | 3/2006 | Orr et al. |
| 7,505,196 B2 | 3/2009 | Nati et al. |
| 8,693,004 B2 | 4/2014 | Chandler et al. |
| 8,917,396 B2 | 12/2014 | Picque et al. |
| 9,207,121 B2 | 12/2015 | Adler |
| 9,659,760 B2 | 5/2017 | Gordon et al. |
| 2011/0043815 A1* | 2/2011 | Giaccari ............... G01J 3/453 356/451 |
| 2013/0342836 A1 | 12/2013 | Newbury et al. |
| 2017/0307443 A1* | 10/2017 | Bekal .................. G01J 3/4338 |
| 2018/0073856 A1* | 3/2018 | Cundiff ............... G01N 21/636 |

OTHER PUBLICATIONS

Picque et al., "Molecular Spectrosocpy with Laser Frequency Combs", Proceedings of the 11th International Conference on Laser Spectroscopy, 2011, pp. 1-10.
Hansch et al., "Laser Spectroscopy and Frequency Combs", Journal of Physics: Conference Serials 467 (2013) p. 1-7.
Ideguchi, et al., "Adaptive real-time dual-comb spectroscopy" Nature Communications 2014 p. 1-8.
Newbury, et al. "Sensitivity of coherent dual-comb spectroscopy" Optics Express, Apr. 12, 2010, vol. 18, No. 8 7929-7945.

* cited by examiner

DUAL-COMB SPECTROSCOPY WITH A FREE-RUNNING BIDIRECTIONALLY MODE-LOCKED FIBER LASER

BACKGROUND

Optical frequency combs (OFCs) are useful tools for many applications including optical clocks, precision frequency/time transfer, low phase noise microwave generation, astronomical spectrograph calibration, molecular spectroscopy, coherent LIDAR, and arbitrary optical/RF waveform generation. The main advantage of OFCs arises from the fact that thousands of highly coherent optical frequencies are accurately and precisely defined with only two degrees of freedom, namely, the carrier-envelop-offset frequency (CEO frequency) and the repetition rate of the femtosecond laser pulse train. Despite years of research and development effort from both academia and industry, OFCs are generally currently available only at leading metrology labs that can build the laser system themselves or have enough resources to purchase expensive commercial OFCs. OFCs may find more widespread use in practical applications if they are less expensive, easier to build, and more robust such that they can work outside of a controlled laboratory environment. This is particularly true for applications needing more than one OFC such as for dual-comb spectroscopy (DCS).

In DCS, two broadband mutually coherent OFCs (at least during the time of measurement) working at the same center frequency but having a slight difference in repetition rates are needed. DCS can achieve high spectral resolution and short acquisition time simultaneously since no moving part is involved. In addition, single-shot, high signal-to-noise ratios over a large spectrum bandwidth have been demonstrated with the use of tightly phase-locked coherent OFCs. One of the ongoing research efforts is focusing on simplifying the experimental setup for a high quality DCS. A notable result in this direction is the adaptive sampling technique reported in T. Ideguchi et al., "Adaptive real-time dual-comb spectroscopy," Nat. Commun. 5, 3375 (2014). It turned out that the demanding phase-locking requirement of the two OFCs can be removed by an adaptive sampling technique using specially designed electronics. Recently, another technique has been demonstrated that allowed DCS of an acetylene gas cell using two free-running mode-locked fiber lasers. The experimental setup is simpler but it did not achieve single-shot measurement due to the poor signal-to-noise. DCS has also been reported with the use of a single mode-locked laser and a Dazzler, but the spectral resolution and noise performance were limited.

DCS is a form of Fourier transform spectroscopy. In order to simplify its requirements, the traditional moving mirror is replaced by sampling one OFC with a second OFC which operates at a slightly different repetition rate. The two combs are typically generated from two different laser cavities so they are not phase coherent. DCS requires the two combs to be phase coherent during the time of measurement since narrow absorption lines would be washed out otherwise. One way to implement DCS in a phase coherent manner is to phase lock the two combs using electronics. Each comb has two degrees of freedom, so four servo locks are needed on top of the knowledge of the CEO frequency for each comb (which typically requires octave spanning supercontinuum generation for f-to-2f detection). This approach is not simple but it works and exhibits the best DCS performance achieved so far.

SUMMARY

In accordance with one aspect of the subject matter described herein, a DCS arrangement is provided for generating the two OFCs from a single laser cavity so that common noise/drifts are cancelled, which should remove the need for complex phase locking apparatus. It is known that a ring fiber laser that can be mode-locked bidirectionally may be used to generate two OFCs. More specifically, in K. Kieu and M. Mansuripur, "All-fiber bidirectional passively mode-locked ring laser," Opt. Lett. 33, 64-66 (2008), a bidirectionally mode-locked laser has been proposed for precision rotation sensing, where it was desirable to have the two laser pulse trains to lock in repetition rate. It was also observed in this reference that the two femtosecond laser pulse trains could have a slightly different repetition rates but the authors did not explore DCS with the laser source at that time.

In one particular implementation, a bidirectional mode-locked fiber laser generates two femtosecond frequency combs (with a small difference in repetition rates) so that they are mutually coherent. Since environmental noise or laser drift are common to both frequency combs they can be cancelled out automatically. For that reason, real-time absorption spectroscopy measurements have been obtained without the need for complex servo locking or post-signal processing with accurate frequency referencing and relatively high signal to noise ratio.

DETAILED DESCRIPTION

Figure 1:
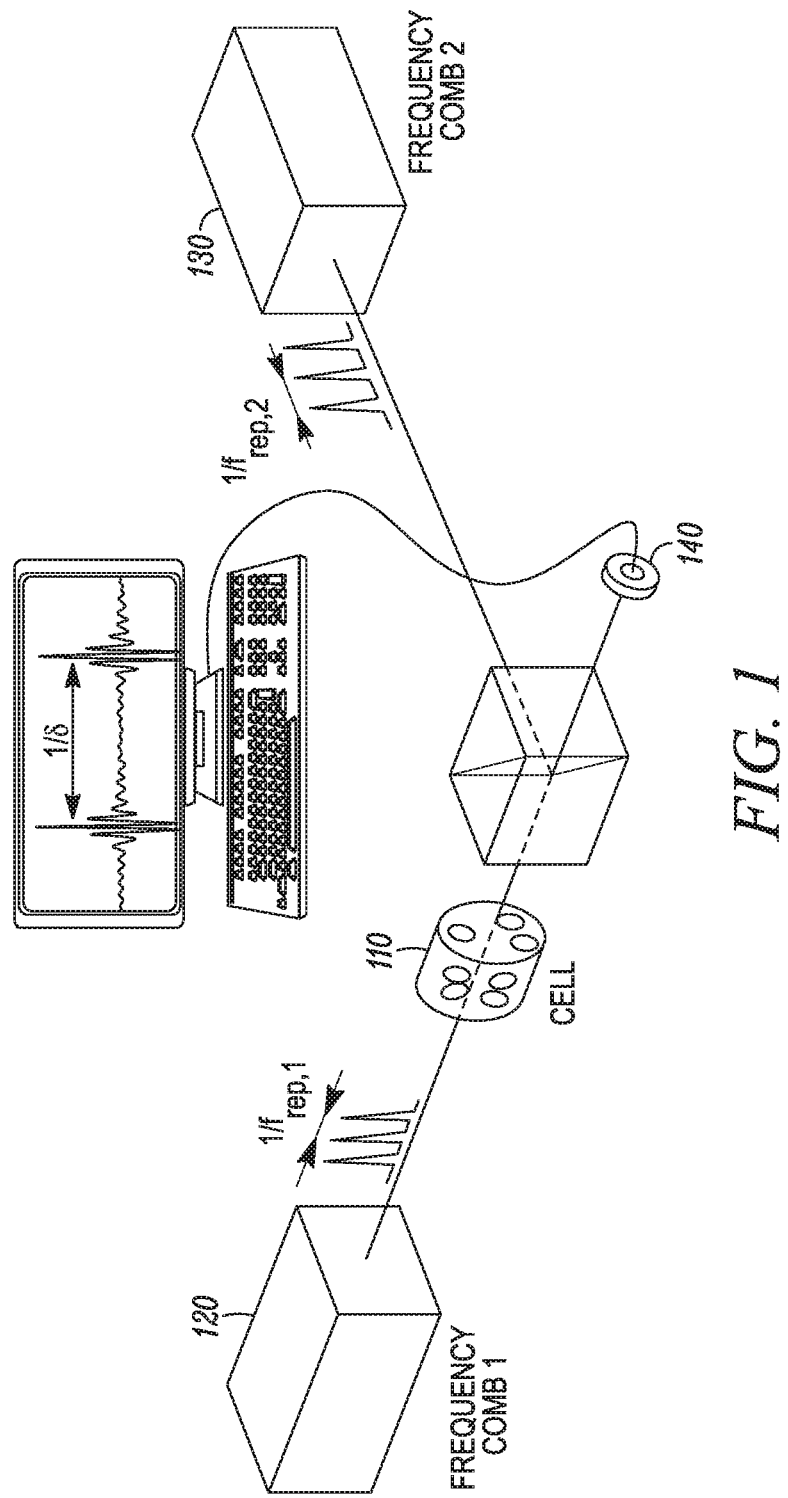
FIG. 1 shows a simplified dual-comb spectroscopy arrangement in which an absorbing sample is interrogated by a frequency comb laser source.

The basic operating principles of dual-comb spectroscopy will be illustrated with reference to FIGS. 1 and 2. FIG. 1 shows a simplified dual-comb spectroscopy arrangement in which an absorbing sample 110 is interrogated by a frequency comb laser source 120. The sample's response encoded by this interrogating comb needs then to be retrieved by a spectrometer. This is achieved by heterodyning the interrogating comb with a second frequency comb laser source 130, which serves as a reference or local oscillator. A fast photodetector 140 then produces an output signal with a comb of radio frequencies due to interference between pairs of optical comb lines.

Figure 2A:
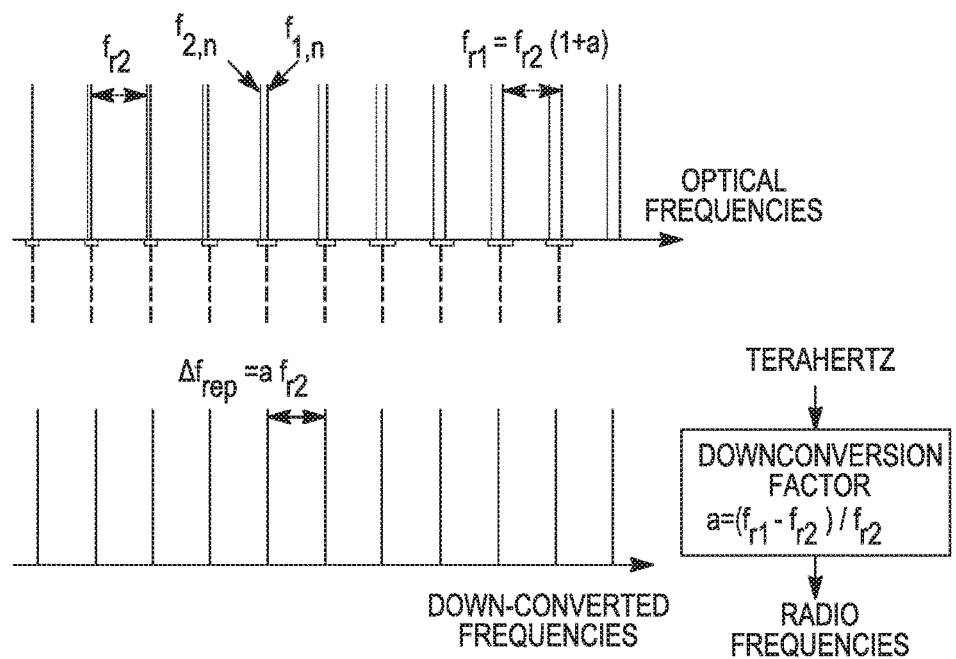
FIG. 2A shows the pulse trains generated by the laser sources of FIG. 1 being down-converted or mapped into the radio frequency (RF) region and FIG. 2B shows the pulse trains generated by the laser sources of FIG. 1 in the time domain.
Figure 2B:
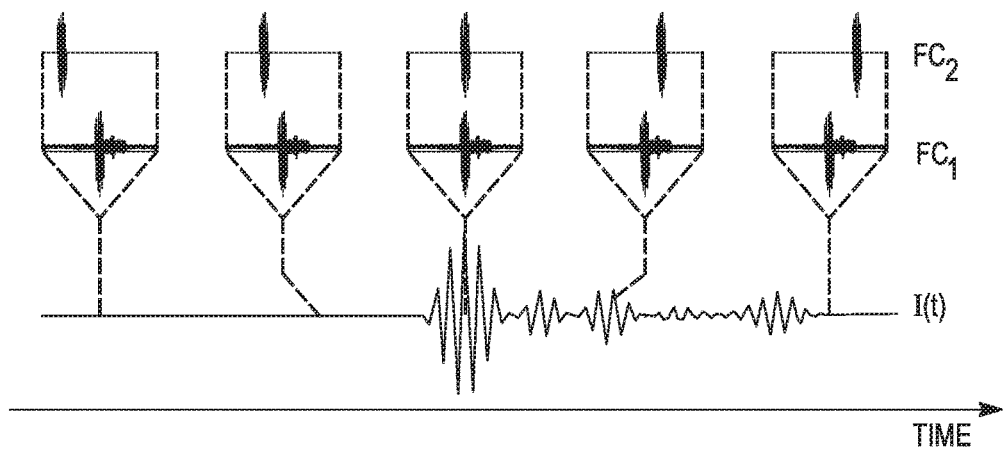

The two frequency combs have slightly different line spacings. As shown in FIG. 2A, in the frequency domain the repetition frequency of the two laser sources 120 and 130 is $f_{r1}$ and $f_{r2}$, respectively, and they differ by $\Delta f_r \ll f_{r1}$. The reference comb 2 with $f_{r2}$ line spacing acts as a local oscillator or multiplexed heterodyne receiver to generate a radio-frequency comb. As further shown in FIG. 2A, the optical spectrum is thus effectively down-converted or mapped into the radio frequency region, where it becomes accessible to fast digital signal processing. FIG. 2B shows the pulse trains generated by the laser sources 120 and 130 in the time domain. The reference comb FC2 pulse train generated by the laser source 130 slowly walks through the interrogating pulse train FC1 generated by the laser source 120 to produce a measurement I(t) of the interrogating electric field. In this way the full complex response of the absorbing sample 110 (i.e., phase and amplitude) with the frequency resolution and accuracy inherent in the comb source.

As described below, a method and apparatus is presented in which the two frequency combs are generated by a single laser cavity, thereby eliminating the need for a complex phase locking apparatus.

Figure 3:
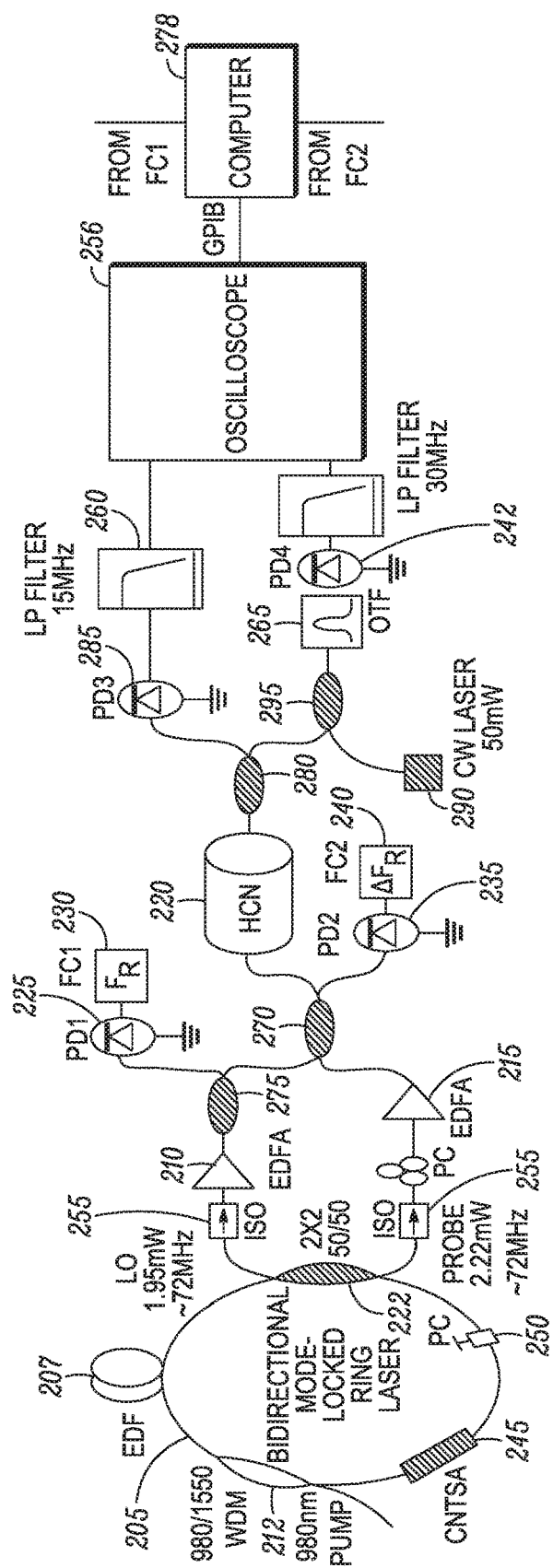
FIG. 3 shows a schematic diagram of one example of a dual-comb spectroscopy (DCS) arrangement that employs a single free-running bidirectionally mode-locked laser.

FIG. 3 shows a schematic diagram of one example of a dual-comb spectroscopy (DCS) arrangement that employs a free-running bidirectionally mode-locked laser such as a bidirectionally mode-locked ring fiber laser 205 that uses a rare-earth doped segment 207 as the gain medium. In one implementation the rare-earth element that is employed is erbium (Er). The single cavity ring fiber laser 205 generates two optical frequency combs (OFCs). The repetition rate difference between the two OFCs may be, in one example, about 60 Hz. The two OFCs are amplified in two separate optical amplifiers 210 and 215 such as Er-doped fiber amplifiers (EDFA) and then combined for DCS on an absorbing sample 220, which in this example is an HCN gas cell. The repetition rate of one OFC is measured with a first photodiode (PD1) 225 and a first frequency counter (FC1) 230. The repetition rate difference is measured with a second photodetector (PD2) 235 and a second frequency counter (FC2) 240. The mode-locked ring fiber laser 205 employs a saturable absorber 245 that is based on carbon nanotubes coated on a fiber taper. Also shown in FIG. 3 are such ancillary components of the mode-locked ring fiber laser 205 such as a polarization controller (PC) 250, a wavelength division multiplexer (WDM) 212 for injecting the pump power into the laser cavity, and a 2×2 50/50 coupler 222 for extracting the two optical frequency combs.

The ring fiber laser 205 can be mode-locked in both the clockwise (CW) and counter-clockwise (CCW) directions by increasing the pump power above the laser threshold. The inline-type polarization controller 250 is used in the cavity to optimize the operation of the laser.

Those of ordinary skill in the art will recognize that the arrangement shown in FIG. 3 is only illustrative of a variety of different DCS arrangements that may employ a bidirectional mode-locked laser. For example, while in FIG. 3 the two OFCs are combined prior to being directed to the absorbing sample 220, in other implementations the two OFCs may be separately directed to the absorbing sample and combined therein. Moreover, the operating frequencies presented below are shown for illustrative purposes only. More generally, the laser may operate at any frequencies that are suitable for interrogating any particular sample.

In general, any pulsed laser source using any suitable technique may be employed in the DCS arrangement to generate the two optical frequency combs. For instance, directly modulated lasers or mode-locked lasers may be used in some embodiments. In a mode-locked laser such as shown in FIG. 3, the various modes oscillate with fixed phases with respect to one another. In this way the laser modes will all periodically constructively interfere with one another, producing an intense burst or pulse of light. Such a laser is said to be mode-locked or phase-locked.

The pulsed laser source may be mode-locked by either an active mode-locking technique or a passive mode-locking technique. In active mode-locking, an external signal drives a modulator that modulates the light in the laser cavity. The modulator is typically located within the laser cavity itself. In passive mode-locking an element is placed in laser cavity which causes self-modulation of the light. For instance, in one example, such as in the ring fiber laser 205 in FIG. 3, the element may be a saturable absorber, which has an intensity dependent transmission response. In general, passive mode-locking may be achieved using others suitable elements instead of a saturable absorber including, for instance, a semiconductor saturable absorber mirror (Sesam) or an arrangement that employs a nonlinear polarization evolution (NPE) mechanism.

In one particular implementation, the two frequency combs operate at about 1557 nm center wavelength with repetition rates of about 72,375,637 Hz and 72,375,697 Hz, corresponding to a $\Delta f_r=60$ Hz detuning frequency. $\Delta f_r$ can be slightly tuned by changing the pump power or adjusting the inline polarization controller 250, for example. The net cavity dispersion is anomalous so the laser generates transform-limited soliton pulses. The average output powers of the CCW (Probe) pulse train and the CW pulse train (local oscillator, LO) were measured to be 1.95 mW and 2.22 mW, respectively. Of course, in some implementations the CCW pulse train may serve as the local oscillator and the CW train may serve as the probe.

Figure 4A:
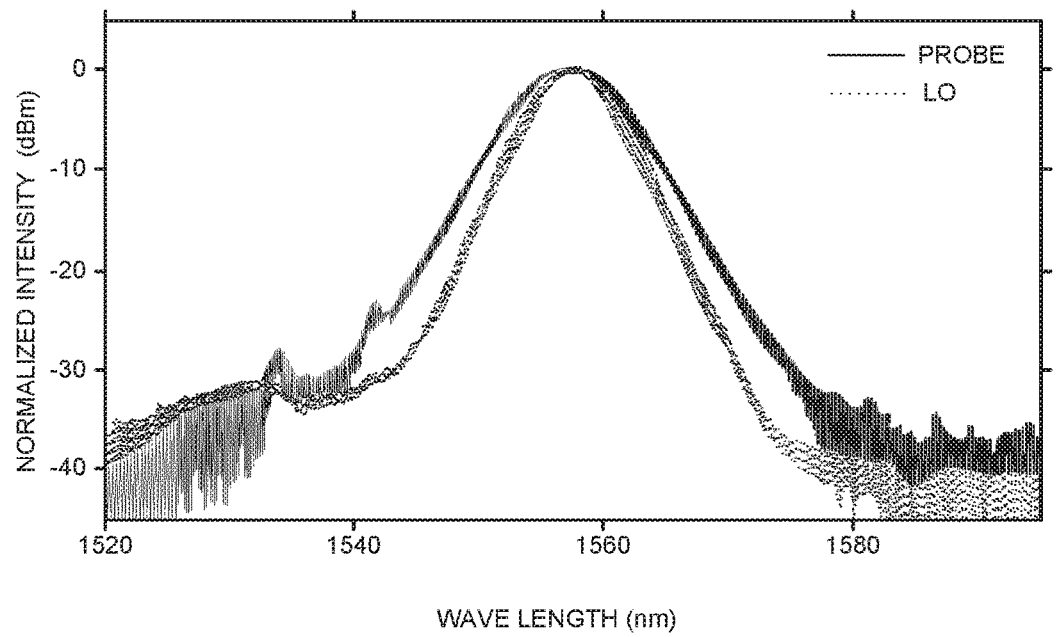
FIG. 4A shows the spectra of the two frequency combs generated by the mode-locked laser of FIG. 3
Figure 4B:
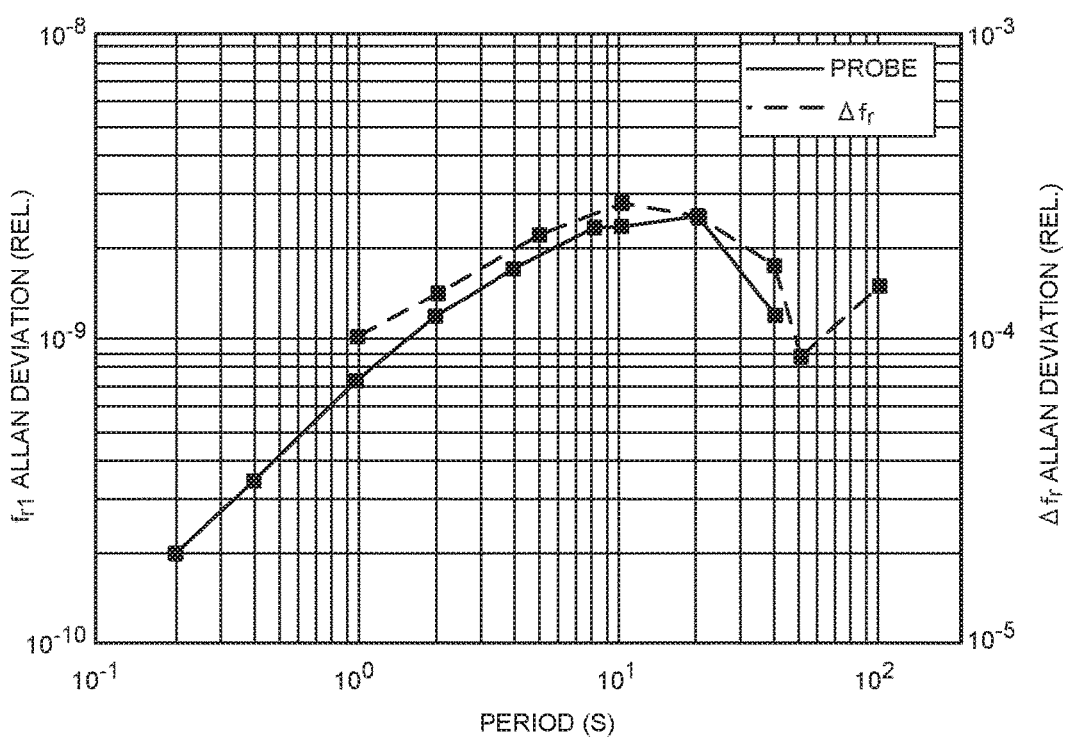
FIG. 4B shows their Allen deviation values.

The spectra of the probe pulse train and the LO pulse train are shown in FIG. 4A. The Allan deviation of the Probe's repetition rate ($f_r$) and the difference in repetition rates between the Probe and LO pulse trains ($\Delta f_r$) were measured with 200 ms and 1 s gating time, respectively. The Allan deviation values of $6 \times 10^{-10}$ for $f_r$ and $10^{-4}$ for $\Delta f_r$, at 1 s period, are shown in FIG. 4B.

In the DCS arrangement of FIG. 3, the combs are first amplified by two separate Er-doped fiber amplifiers (EDFAs) 210 and 215 and then combined with a 2×2, 50/50 coupler 270. The FWHM spectral bandwidths of the pulses are broadened to about 18 nm in the amplifiers (Probe~30 mW, PLO~16 mW after amplifications). The optical spectra of the pulses are intentionally broadened in order to cover more absorption lines of HCN gas in the DCS experiment described below. A small portion of the CCW pulse train is extracted by a 90/10 fiber splitter 225 and used for repetition rate measurement using PD1 225 and a 12 digit frequency counter 230. One part of the combined OFCs is used after the 50/50 fiber coupler 270 to detect the difference in the laser repetition rates, again using PD2 235, a low-pass RF filter, and a frequency counter 240. The other part of the combined OFCs pass through the absorbing sample 220, which in one illustrative implementation is a 100 Torr, 16.5 cm long HCN gas cell (available from Wavelength Reference Inc.) for absorption measurement. The output from the gas cell is split equally into two paths by 50/50 fiber coupler 280. The laser beam in one path is detected by a 100 MHz photodiode (PD3) 285 and then low-pass filtered by filter 260 to avoid aliasing (DC-30 MHz) before being digitized with an oscilloscope 256. The beam in the other path is combined with the output from a single frequency CW fiber laser 290 (available from Koheras Inc.) using a 1×2, 90/10 coupler 295 in order to provide absolute frequency calibration. The single frequency CW fiber laser 290 has a very narrow linewith of less than 1 kHz ($\lambda_{CW}$=1549.513 nm).

After being optically filtered with a 1 nm FWHM passband band-pass tunable filter 265, the beat notes between the CW fiber laser 290 and one of each comb's nearby modes are detected by another 100 MHz photodiode (PD4) 242. The time-traces of the interferogram (from PD3 285) and the time domain mixing signal (from PD4 242) are acquired by a digital oscilloscope with real-time Fast Fourier Transform (FFT) capability. The oscilloscope 256 and frequency counters are connected to a PC 278 and a customized Lab VIEW program is used to control the acquisition parameters and to save data. The interferogram, the repetition rate, the difference in the repetition rates, and the two beatnotes between the CW laser and the two combs can all be simultaneously recorded in each measurement. These four parameters are then used for accurate frequency referencing without the need to detect the CEO frequency of each comb.

Figure 5A:
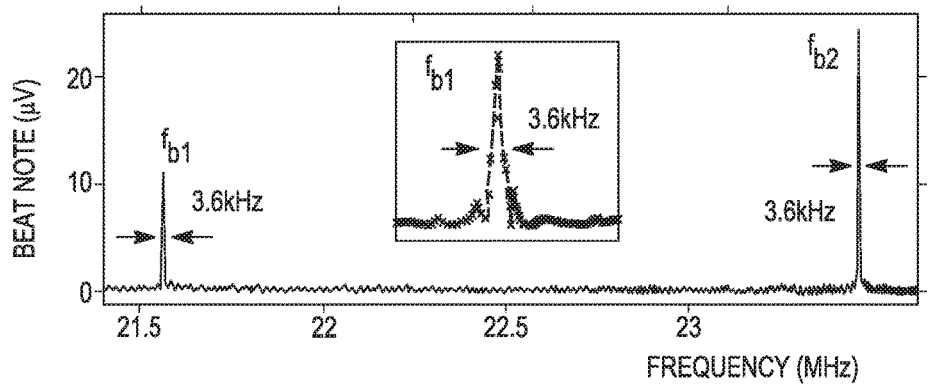
FIG. 5A shows representative beatnotes recorded by the Fast Fourier Transform (FFT) of the voltage signal between a CW laser and one of the nearby modes of the combs output from the absorbing sample.
Figure 5B:
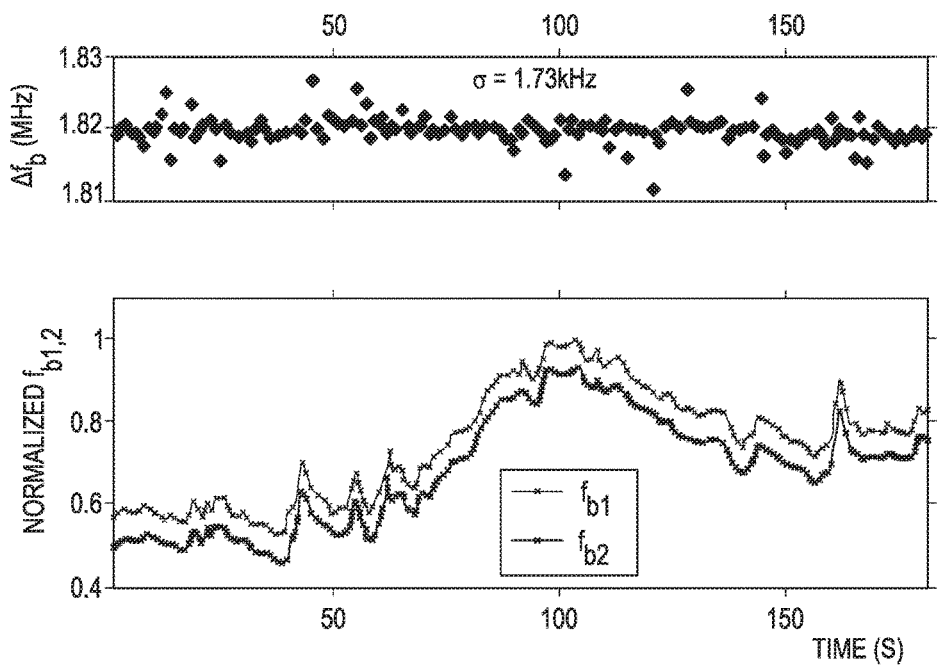
FIG. 5B shows the measured time evolution of $f_{b1}$, $f_{b2}$ and $\Delta f_b$ for 180 successive single shot acquisitions.

FIG. 5A shows representative beatnotes recorded by FFT of the voltage signal generated by PD4 242. The FWHM linewidth of the OFCs denoted $f_{b1}$ and $f_{b2}$ were measured at ~3.6 kHz with 610 Hz resolution, which was defined by the acquisition time window. This indicates that the two OFCs generated by the bidirectionally mode-locked fiber laser 205 have low noise performance. The temporal dynamics of the beatnotes were also recorded to get an idea about the drift experienced by the laser modes in free-running regime. In particular, FIG. 5B shows the measured time evolution of $f_{b1}$, $f_{b2}$ and $\Delta f_b$ for 180 successive single shot acquisitions. The observed drift is quite significant (in the order of 280 kHz/second) but, interestingly, the separation between the two beatnotes ($\Delta f_b = f_{b1} - f_{b2}$ or the separation between the two neighboring modes of each OFC) does not change that much. The mean value of $\Delta f_b$ was about 1.82 MHz with 1.73 kHz standard deviation. It can be concluded from the results of this measurement that the two OFCs drift in close synchronization with each other. The explanation for this experimentally observed behavior is the fact that they share the same cavity. This is a primary reason why DCS can be achieved using this laser source in free running mode.

Figure 6A:
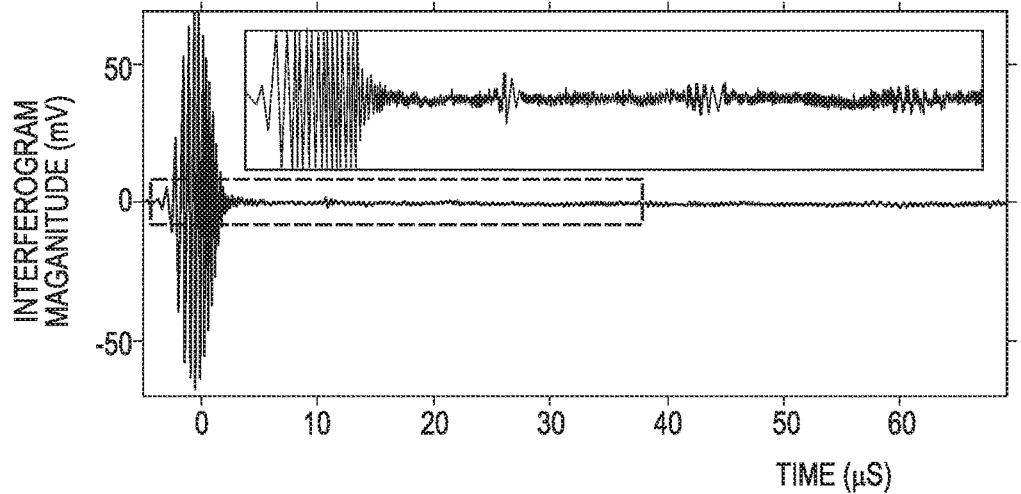
FIG. 6A shows a portion of a single-shot and a zoom-in region at the center of the burst interferogram output from the absorbing sample.
Figure 6B:
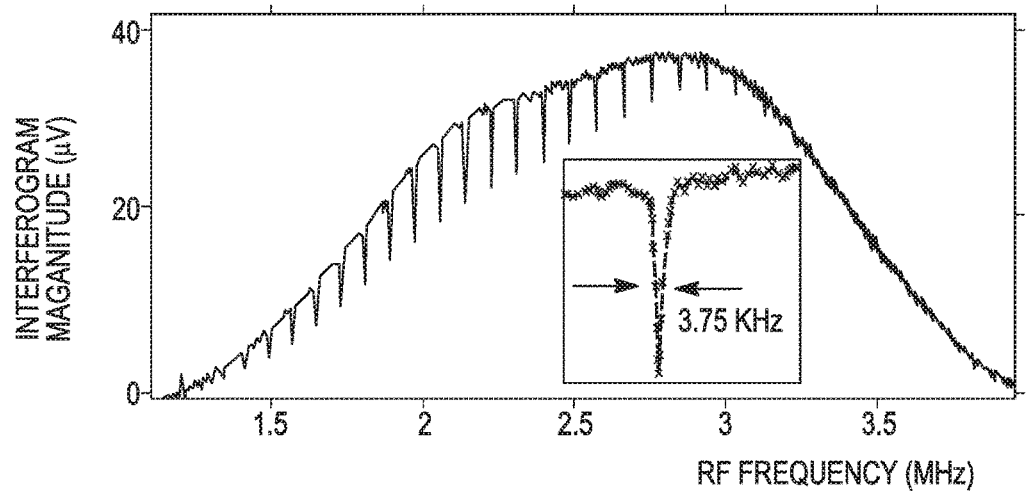
FIG. 6B shows the absorption spectrum of the sample in the RF domain.

FIG. 6A shows a portion of a single-shot and a zoom-in region at the center of the burst interferogram (recorded by PD3). The acquisition time window was set to 1.28 ms with about a 78 MHz sampling rate resulting in about a 937 Hz spectral resolution. The ringing free-induction-decay (FID) signals from HCN molecules are readily visible. The time-domain signal-to-noise-ratio (SNR) defined by the ratio of interferogram peak signal to the standard deviation of the background noise calculated for the area just before the center burst was about 329. FIG. 6B shows the absorption spectrum of the HCN cell in the RF domain, which is just the Fourier transform of the time domain interferogram.

The optical frequency v can be calculated from the RF domain $f^{RF}$ using the following equation:

$$v = \pm (f^{RF} - \Delta f_b)\frac{f_{r1}}{\Delta f_r} + v_{CW} - f_{b1}$$

Where $f_{r1}$ and $\Delta f_r$ are the repetition rate of the probe pulse train and the repetition rate difference, respectively and $\Delta f_b$ is the difference between the beating of the CW laser with the nearest tooth of each comb ($f_{b1}-f_{b2}$). The sign of $f^{RF}$ is changed as needed for correct frequency calibration. A derivation of this equation may be found in the Appendix.

The selection of sampling rate and acquisition time window enables enough sampling points to resolve the absorption lines in the P-band of HCN. A zoom-in example of an absorption line is represented in the inset of FIG. 6B.

Figure 7:
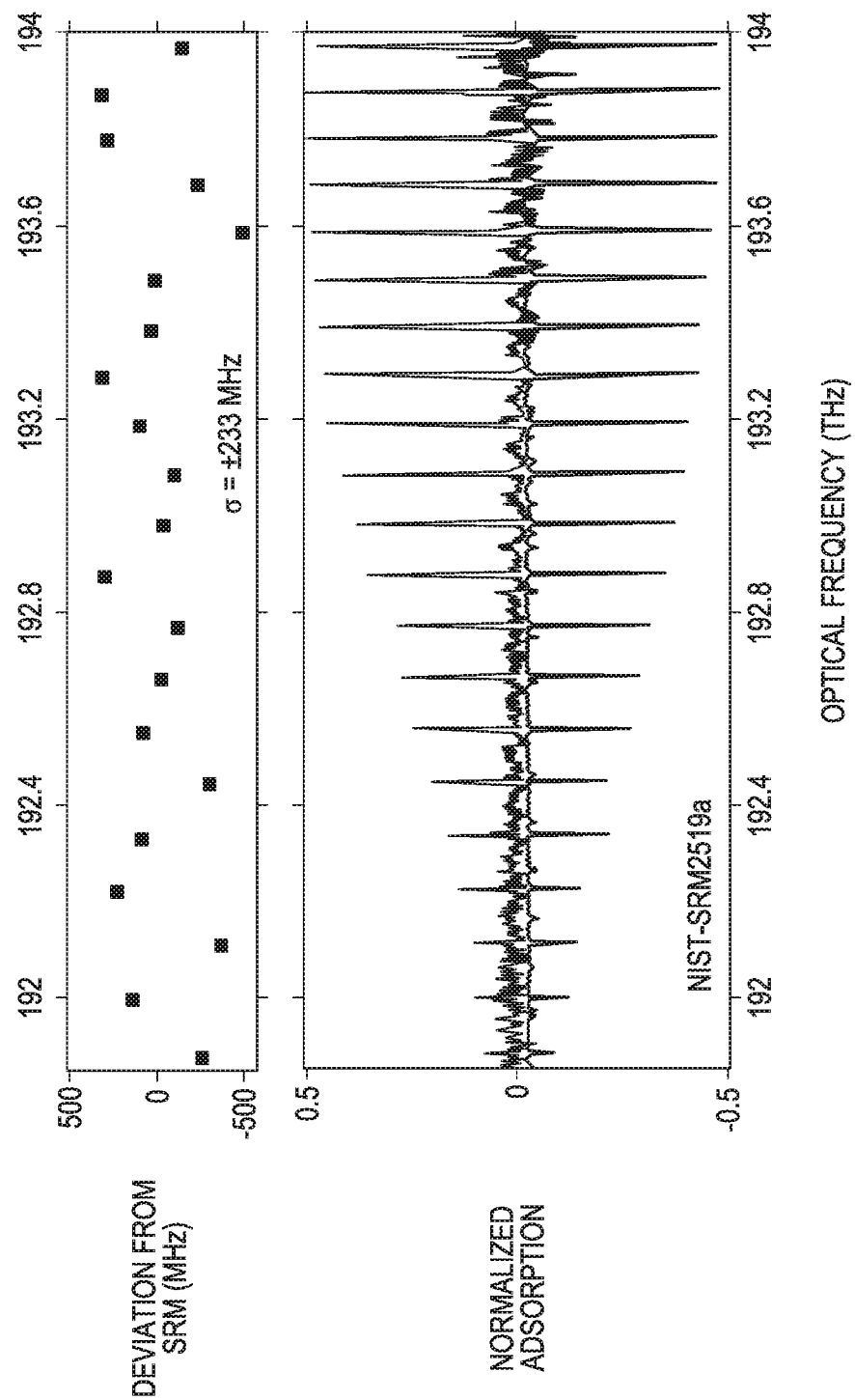
FIG. 7 presents the 21 extracted most intense absorption lines in the P-band of the sample in the NIR region (upper lines in the bottom panel of FIG. 7) and the peak absorption values retrieved from the National Institute of Standard and Technology (NIST) database (bottom lines in the bottom panel of FIG. 7).

In order to normalize the absorption spectrum shown in FIG. 6B, a smooth function in MATLAB is applied and then the absorption spectrum is normalized by the smoothed function, resulting in a spectrum with a flat baseline. FIG. 7 presents the 21 extracted most intense absorption lines in the P-band of HCN in the NIR region (see the upper lines in the bottom panel of FIG. 7), which have about a 6% deviation compared to the peak absorption values retrieved from the National Institute of Standard and Technology (NIST) database (see the bottom lines in the bottom panel of FIG. 7). Furthermore, as shown in the top panel of FIG. 7, the standard deviation of about 233 MHZ for the center-peak frequencies was measured. This deviation can be attributed to the drift of the center frequency of the free running CW laser. This can be improved by employing a wavemeter to record $v_{CW}$ at the time of measurement. The CW laser can also be locked to a narrow molecular absorption line to avoid frequency drift. Moreover, a very small variation in $\Delta f_r$ can result in a significant error in the optical frequency conversion from RF domain due to the small value detuning frequency of 60 Hz relative to the repetition frequency of 72 MHz. This discrepancy can be solved by referencing the frequency counters and the digital oscilloscope to a highly precise rubidium oscillator.

The single-shot measurement shown in the figures can readily resolve the absorption lines of HCN where there is no need for optical phase-locking of the combs or employing elaborate adaptive sampling and complicated electronics in detection circuit. The signal-to-noise ratio of 28 in the optical domain was defined as the ratio of the most intense peak absorption line to the corresponding standard deviation of the noise floor. Finally, the noise equivalent absorption (NEA) was calculated by using:

$$NEA = \frac{1}{L \cdot \frac{S}{N}}\sqrt{T}$$

Where L is the gas cell length, S/N is the signal-to-noise ratio and T is the acquisition time window. An NEA of 6.6×10$^{-6}$ cm$^{-1}$ Hz$^{-1/2}$ was recorded based on measured SNR and chosen T.

In conclusion, two OFCs have been generated from a single ring fiber laser cavity and used as the source for DCS. Narrow absorption lines of HCN in the P-band have been resolved in real-time without the need for optical phase-locking of the two OFCs or complex electronic signal processing techniques. This simple, robust and all-fiber DCS design can replace other complex gas sensing arrangements. Moreover, spectral broadening of the laser source and other nonlinear mixing techniques can be used to cover other optical spectral regions of interest.

Although the subject matter has been described in language specific to structural features and/or methodological acts, it is to be understood that the subject matter defined in the appended claims is not necessarily limited to the specific features or acts described above. Rather, the specific features and acts described are disclosed as example forms of implementing the claims.

Appendix—Rf-To-Optical Frequency Conversion

As previously mentioned, the RF domain absorption spectrum of HCN is directly recorded by the Fast Fourier Transform (FFT) of the time domain interferogram generated by beating the two OFCs on a photodetector. The RF spectrum needs to be converted into the optical domain using the measured characteristics of the dual-comb source, including the repetition rate ($f_r$), the difference in the repetition rates ($\Delta f_r$) and the beatnotes of the CW laser with the two combs ($f_{b1}$, $f_{b2}$). Here, the equation for the conversion of the RF domain data into the optical domain will be described in detail.

The longitudinal modes of the frequency combs can be described as:

$$v_p^1 = f_{CEO1} + p f_{r1}$$

$$v_p^2 = f_{CEO2} + q f_{r2} \quad (1)$$

where p and q are the mode indices of comb1 and comb2, respectively. $f_{CEO1}$, $f_{CEO2}$ are the carrier-to-envelop offset frequencies and $f_{r1}$, $f_{r2}$ are the repetition rates of the combs. The basic idea of dual-comb spectroscopy is based on interfering two combs with a slight difference in repetition rates $\Delta f_r$. An RF comb (after low-pass filtering) is formed from the beating of the corresponding neighbor modes of the two combs. To ensure a one-to-one mapping of the RF comb to the optical comb, it is required that $\Delta v_{comb}/f_r < f_r/(2\Delta f_r)$, or $\Delta v_{comb} < f_r^2/(2\Delta f_r) \sim 43$ THz. The spectral bandwidth of the pulses (~1 THz) emitted from the laser source is much smaller than 43 THz and thus meets the Nyquist requirement. The RF comb corresponding to the full allowed bandwidth would be expanding from zero to $f_r/2$ (Note that $\Delta f_r$ is typically very small compared to the repetition of either combs). In the example presented herein, the RF comb spans from ~1 MHz to ~4 MHz (see FIG. 6B). Similar to an optical comb the RF comb can be also described as:

$$v_s^{RF} = f_{CEO}^{RF} + s \cdot \Delta f_r \quad (2)$$

where s is an integer and $f_{CEO}^{RF}$ ($<\Delta f_r$) is the corresponding RF 'carrier-to-envelop offset frequency'. In general, it can be assumed that $f_{CEO}^{RF}$ is the beating between two comb teeth: one from comb 1 and the other from comb 2 with mode indexes n and n', respectively. Since it can be assumed that $f_{r1} > f_{r2}$ then n' can be written as n'=n+k, where k is a positive integer number. We then have:

$$v_n^1 - v_{n'}^2 = v_n^1 - v_{n+k}^2 \quad (3)$$
$$= (f_{CEO1} + n f_{r1}) - (f_{CEO2} + (n+k) f_{r2})$$
$$= f_{CEO1} - f_{CEO2} + n \Delta f_r - k f_{r2}$$
$$= \Delta f_{CEO} + n \Delta f_r - k f_{r2} = r_n < \Delta f_r$$

Figure 8:
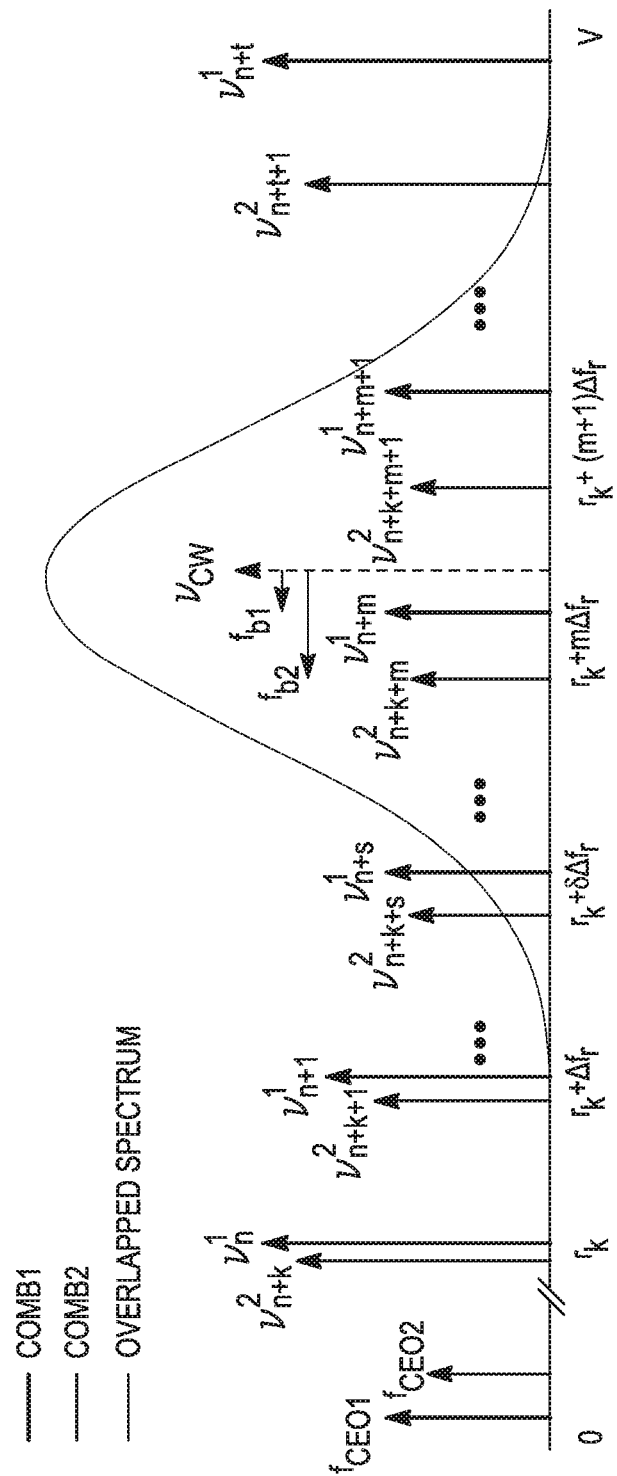
FIG. 8 shows the beating between pairs of the modes of the frequency combs in the optical domain to form the down-converted RF comb.

According to FIG. 8, which shows the beating between pairs of the modes of the frequency combs in the optical domain to form the down-converted RF comb, the down-converted RF comb modes can be formulated as:

$$v_{n+s}^1 - v_{n+k+s}^2 = (f_{CEO1} + (n+s) f_{r1}) - (f_{CEO2} + (n+k+s) f_{r2}) \quad (4)$$
$$= [\Delta f_{CEO} + n \Delta f_r - k f_{r2}] + s \Delta f_r$$
$$\xrightarrow{eq(S2)} = r_n + s \Delta f_r$$

Here, $f_{CE}^{ORF} + s \cdot \Delta f_r$ (s=0, 1, 2, . . . ) are the RF comb teeth which is defined as $v_s^{RF}$ above.

The beating between the CW laser and the corresponding nearest optical modes of the OFCs creates two RF beat notes $f_{b1}$ and $f_{b2}$. According to FIG. 8 the difference of these RF beat notes is:

$$\Delta f_b = |f_{b1} - f_{b2}| \quad (5)$$
$$= |(v_{CW} - v_{n+m}^1) - (v_{CW} - v_{n+k+m}^2)|$$
$$= v_{n+m}^1 - v_{n+k+m}^2$$
$$\xrightarrow{eq(S3)} = r_n + m \Delta f_r$$

By knowing $\Delta f_b$, the optical mode $v_{n+s}^1$ can be calculated as:

$$v_{n+s}^1 = f_{CEO1} + (n+s) f_{r1} \quad (6)$$
$$= [f_{CEO1} + (n+m) f_{r1}] - (n+m) f_{r1} + (n+s) f_{r1}$$
$$\xrightarrow{Fig.S2} = v_{n+m}^1 + (s-m) f_{r1}$$
$$= v_{n+m}^1 + [(r_n + s \Delta f_r) - (r_n + m \Delta f_r)] \frac{f_{r1}}{\Delta f_r}$$
$$\xrightarrow{Eq(S4)} v_{n+s}^1 = (f_{rf,s} - \Delta f_b) \frac{f_{r1}}{\Delta f_r} + v_{n+m}^1$$

All the parameters defining $v_{n+s}^1$ can be measured by using an oscilloscope and frequency counters except $v_{n+m}^1$, which is the nearest mode of comb1 to the CW laser. If this mode $$n + m = \frac{v_{CW} - f_{b1} - f_{CEO1}}{f_{r1}}$$

can be defined with enough precision then $v_{n+q}^1$ can be obtained. According to equation (F1), $v_{n+m}^1$ can be calculated precisely through the knowledge of $f_{CEO1}$ and the optical domain mode index: n+m. $f_{CEO1}$ can be measured using a f-to-2f interferometer. By measuring $f_{CEO1}$, the integer mode index n+m can be calculated unambiguously as follows:

$$n + m = \frac{v_{CW} - f_{b1} - f_{CEO1}}{f_{r1}}$$

$f_{b1}$ can be measured by beating the CW laser and comb1. Furthermore, $v_{CW}$ and $f_{r1}$ can be measured by using a wavemeter and a frequency counter, respectively. Therefore, $v_{n+m}^1$ can be extracted with accuracy which is limited by the precision of the instruments. Alternatively, one can estimate $v_{n+m}^1$ by just measuring $v_{CW}$ and $f_{b1}$ instead of $f_{CEO1}$. This estimation is readily derived from equation (6), i.e. $v_{n+m}^1 =$ $(n+m)f_{r1}+f_{CEO1}=v_{CW}-f_{b1}$. However, this approach requires the knowledge of $v_{CW}$. This can be done quite easily with a wavemeter.

The invention claimed is:

1. A method of interrogating an absorbing sample, comprising:
   using a mode-locked laser mode-locked in both a clockwise (CW) and a counter-clock wise (CCW) direction to generate first and second optical pulses having different repetition rates, one of the first and second optical pulses being directed in a CW direction and the other of the first and second optical pulses being directed in the CCW direction;
   transmitting the first optical pulses through the absorbing sample to probe the absorbing sample while transmitting the second optical pulses through the absorbing sample to act as a local oscillator; and
   detecting an interference pattern produced by interference between the first and second optical pulses after traversing the absorbing sample.

2. The method of claim 1, wherein the first and second optical pulses are transform-limited soliton pulses.

3. The method of claim 1, further comprising optically amplifying the first and second optical pulses before transmission through the absorbing sample.

4. The method of claim 3, wherein optically amplifying the first and second optical pulses includes spectrally broadening the first and second optical pulses.

5. The method of claim 1, further comprising detecting a portion of the second optical pulses prior to transmission through the absorbing sample to determine a repetition rate of the second optical pulses.

6. The method of claim 1, further comprising combining the first and second optical pulses prior to transmission of the first and second optical pulses through the absorbing sample.

7. The method of claim 6, further comprising detecting a portion of the combined first and second optical pulses to determine a difference in repetition rates between the first and second optical pulses.

8. The method of claim 1, further comprising combining a single frequency, continuous-wave (CW) signal with a portion of an optical signal produced by the interference between the first and second optical pulses after traversing the absorbing sample to obtain an absolute frequency reference.

9. The method of claim 1, wherein the mode-locked laser is mode-locked fiber laser.

10. The method of claim 9, wherein the mode-locked fiber laser includes an erbium-doped fiber gain medium.

11. The method of claim 9, wherein the mode-locked fiber laser includes a polarization controller for adjusting a repetition rate of the first and second optical pulses.

12. A method for performing absorption spectroscopy, comprising:
   generating first and second optical frequency combs from a single bidirectional mode-locked laser, the first and second optical frequency combs having different repetition rates,
   transmitting the first and second optical frequency through an absorbing sample; and
   obtaining an interferogram arising from interference between the first and second optical frequency combs after traversing the absorbing sample.

13. The method of claim 12, further comprising determining a repetition rate of the first and second optical frequency combs, a difference in the repetition rate of the first and second optical frequency combs and an absolute frequency reference.

14. The method of claim 12 wherein generating the first and second optical frequency combs includes generating the first and second optical frequency combs in a ring laser source such that the first and second optical frequency combs are propagating in opposite rotational directions.

15. The method of claim 12, further comprising optically amplifying the first and second optical frequency combs before transmission through the absorbing sample.

16. The method of claim 15, wherein optically amplifying the first and second optical frequency combs includes spectrally broadening the first and second optical frequency combs.

17. A dual-comb spectroscopy system, comprising:
   a pulsed laser source having a common laser cavity configured to generate first and second optical pulse trains having different repetition rates, one of the first and second optical pulse trains being directed in a CW direction and the other of the first and second optical pulses being directed in the CCW direction;
   an optical coupling arrangement for (i) extracting the first optical pulse train from the common laser cavity and directing the first optical pulse train through an absorbing sample to probe the absorbing sample and (ii) extracting the second optical pulse train from the common laser cavity and directing the second optical pulse train through the absorbing sample to act as a local oscillator; and
   a first photodetector for detecting an interference pattern produced by interference between the first and second optical pulses after traversing the absorbing sample.

18. The dual-comb spectroscopy system of claim 17, further comprising first and second optical amplifiers for optically amplifying the first and second optical pulse trains, respectively, prior to transmission through the absorbing sample.

19. The dual-comb spectroscopy system of claim 18, wherein the first and second optical amplifiers are configured to spectrally broaden the first and second optical pulse trains.

20. The dual-comb spectroscopy system of claim 17, further comprising a second photodetector for detecting a portion of the second optical pulse train prior to transmission through the absorbing sample to determine a repetition rate of the second optical pulse train.

21. The dual-comb spectroscopy system of claim 17, wherein the optical coupling arrangement further comprises an optical coupler for combining the first and second optical pulse trains prior to transmission of the first and second optical pulse trains through the absorbing sample.

22. The dual-comb spectroscopy system of claim 20, wherein the optical coupling arrangement further comprises an optical coupler for combining the first and second optical pulse trains prior to transmission of the first and second optical pulse trains through the absorbing sample.

23. The dual-comb spectroscopy system of claim 22, further comprising a third photodetector for detecting a portion of the combined first and second optical pulse trains to determine a difference in repetition rates between the first and second optical pulses.

24. The dual-comb spectroscopy system of claim 17, further comprising a continuous-wave (CW) laser source and an optical coupler for combining a single frequency, continuous-wave (CW) signal with a portion of an optical signal produced by the interference between the first and second optical pulse trains after traversing the absorbing sample to obtain an absolute frequency reference.

25. The dual-comb spectroscopy system of claim 17, wherein the pulsed laser source is a mode-locked laser.

26. The dual-comb spectroscopy system of claim 17, wherein the mode-locked laser is a passively mode-locked laser.

* * * * *